US00PP16527P2

(12) United States Plant Patent
Schräder

(10) Patent No.: US PP16,527 P2
(45) Date of Patent: May 9, 2006

(54) ***NEMESIA* PLANT NAMED 'SUMNEM 03'**

(50) Latin Name: *Nemesia caerulea*
Varietal Denomination: Sumnem 03

(76) Inventor: Ralf Schräder, Karl-Leisner-Str. 15, D-59348 Lüdinghausen (DE)

( * ) Notice: Subject to any disclaimer, the term of this patent is extended or adjusted under 35 U.S.C. 154(b) by 36 days.

(21) Appl. No.: 10/959,874

(22) Filed: Oct. 6, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Nemesia* plant named 'Sumnem 03', characterized by its upright to outwardly spreading and compact plant habit; freely branching habit; short internodes; dense and bushy growth habit; early flowering habit; and numerous light purple-colored flowers with violet-colored stripes.

1 Drawing Sheet

Botanical classification/cultivar designation: *Nemesia caerulea* cultivar Sumnem 03.

BACKGROUND OF THE INVENTION

The present invention relates to a new and distinct cultivar of *Nemesia* plant, botanically known as *Nemesia caerulea* and referred to by the name 'Sumnem 03'.

The new *Nemesia* is a product of a planned breeding program conducted by the Inventor in Lüdinghausen, Germany. The objective of the program is to create new upright, vigorous and early-flowering *Nemesia* cultivars with numerous flowers and unique flower colors.

The new *Nemesia* originated from a cross-pollination made by the Inventor of a proprietary *Nemesia caerulea* selection identified as Seedling 12, not patented, as the female, or seed, parent with a proprietary *Nemesia caerulea* selection identified as Seedling 5, not patented, as the male, or pollen, parent in April, 2002. The cultivar Sumnem 03 was discovered and selected by the Inventor as a flowering plant within the progeny of the stated cross-pollination in a controlled environment in Lüdinghausen, Germany in March, 2003.

Asexual reproduction of the new *Nemesia* by terminal cuttings in a controlled environment in Lüdinghausen, Germany since March, 2003, has shown that the unique features of this new *Nemesia* are stable and are reproduced true to type in successive generations.

SUMMARY OF THE INVENTION

The new *Nemesia* has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Sumnem 03' and distinguish 'Sumnem 03' as a new and distinct cultivar:

1. Upright to outwardly spreading and compact plant habit.
2. Freely branching habit.

3. Short internodes; dense and bushy growth habit.
4. Early flowering habit.
5. Numerous light purple-colored flowers with violet-colored stripes.

Plants of the new *Nemesia* differ primarily from plants of the female parent selection in flower color as flowers of plants of the female parent selection do not have violet-colored stripes.

Plants of the new *Nemesia* differ primarily from plants of the male parent selection in the following characteristics:

1. Plants of the new *Nemesia* are more compact than plants of the male parent selection.
2. Plants of the new *Nemesia* have stronger lateral branches than plants of the male parent selection.

Plants of the new *Nemesia* can be compared to plants of the cultivar Pencand, disclosed in U.S. Plant Pat. No. 14,730. In side-by-side comparisons conducted in Lüdinghausen, Germany, plants of the new *Nemesia* differed from plants of the cultivar Pencand in the following characteristics:

1. Plants of the new *Nemesia* were more compact than plants of the cultivar Pencand.
2. Plants of the new *Nemesia* were more upright than and not as outwardly spreading as plants of the cultivar Pencand.
3. Plants of the new *Nemesia* flowered about one to two weeks earlier than plants of the cultivar Pencand.
4. Plants of the new *Nemesia* had smaller flowers than plants of the cultivar Pencand.
5. Flowers of plants of the new *Nemesia* had violet-colored stripes whereas flowers of plants of the cultivar Pencand did not have violet-colored stripes.

BRIEF DESCRIPTION OF THE PHOTOGRAPH

The accompanying colored photograph illustrates the overall appearance of the new *Nemesia,* showing the colors as true as it is reasonably possible to obtain in colored reproductions of this type. Colors in the photograph may differ slightly from the color values cited in the detailed botanical description which accurately describe the colors of the new *Nemesia.* The photograph comprises a side perspective view of a typical plant of 'Sumnem 03' grown in a hanging basket container.

DETAILED BOTANICAL DESCRIPTION

The aforementioned photograph and following observations and averaged measurements describe plants grown in Lüdinghausen, Germany, in an outdoor nursery during the spring and summer with day temperatures ranging from 16 to 24° C., night temperatures ranging from 8 to 12° C. and light levels ranging from 25,000 to 45,000 lux. After rooting, plants were grown for about four months in hanging basket containers. Plants were pinched once. Color references are made to The Royal Horticultural Society Colour Chart, 2001 Edition, except where general terms of ordinary dictionary significance are used.

Botanical classification: *Nemesia caerulea* cultivar Sumnem 03.

Parentage:

*Female parent.*—Proprietary *Nemesia caerulea* selection identified as Seedling 12, not patented.

*Male parent.*—Proprietary *Nemesia caerulea* selection identified as Seedling 5, not patented.

Propagation:

*Type.*—By vegetative cuttings.

*Time to initiate roots, summer.*—About 7 days at 18° C.

*Time to initiate roots, winter.*—About 8 to 9 days at 18° C.

*Time to develop roots, summer.*—About 16 days at 18° C.

*Time to develop roots, winter.*—About 24 days at 18° C.

*Root description.*—Fine, fibrous; freely branching; 162C in color.

Plant description:

*General appearance.*—Upright to outwardly spreading and compact plant habit. Freely branching, typically about six to eight primary lateral branches each with numerous secondary and tertiary lateral branches. Short internodes; dense and bushy growth habit. Numerous light purple-colored zygomorphic flowers with violet-colored stripes. Moderately vigorous growth habit.

*Plant height.*—About 25 to 30 cm.

*Plant diameter or spread.*—About 20 to 25 cm.

*Lateral branches.*—Length: About 20 cm. Diameter: About 2 to 3 mm. Internode length: About 2.5 to 4 cm. Strength: Strong. Texture: Smooth, glabrous. Color: 144A.

*Foliage description.*—Arrangement: Opposite, simple. Shape: Lanceolate. Apex: Acute. Base: Obtuse. Length: About 2.5 to 3.5 cm. Width: About 1 to 1.5 cm. Margin: Slightly serrate. Texture, upper and lower surfaces: Smooth, glabrous. Venation pattern: Pinnate, arcuate. Petiole length: About 3 to 4 mm. Petiole diameter: About 1 mm. Petiole texture, upper and lower surfaces: Smooth, glabrous. Color: Developing leaves, upper surface: 137A. Developing leaves, lower surface: 138A. Fully expanded leaves, upper surface: 137A. Fully expanded leaves, lower surface: 138B. Venation, upper surface: 139A. Venation, lower surface: 144A. Petiole, upper surface: 144A. Petiole, lower surface: 144B.

Flowering description:

*Arrangement/appearance.*—Zygomorphic solitary flowers arranged on terminal racemes; flowering acropetally towards apex. Flowers bilabiate with nectar spur. Flowers face upright to outwardly. Flowers last about eight to ten days on the plant. Flowers not persistent.

*Natural flowering season.*—Natural flowering season is early spring to fall in northern Europe; flowering continuous during this period. Early flowering, plants start flowering about five to six weeks after pinching.

*Quantity of flowers.*—Freely flowering with about 22 to 28 flowers and flower buds per raceme at one time.

*Fragrance.*—Floral-like; faint.

*Inflorescence length.*—About 12 to 15 cm.

*Inflorescence diameter.*—About 3 to 3.5 cm.

*Flower diameter.*—About 2 to 2.5 cm.

*Flower depth.*—About 2 to 2.2 cm.

*Flower buds.*—Shape: Round. Length: About 2 mm. Diameter: About 2 mm. Color: 138A.

*Petals.*—Arrangement/shape: Five petals. Four upper petals are fused at base to form an upright lobed and arched banner lip; lower petal modified into a larger lip with nectar spur and convex oval protuberance which serves as pollinator nectar guide and landing platform. Shape: Oval to obovate. Apex: Rounded. Margin: Entire. Length: Upper lip petals: About 1.5 to 1.7 cm. Lower lip petal: About 1 to 1.1 cm. Width: Upper lip petals: About 4 to 7 mm. Lower lip petal: About 1 cm. Texture, upper and lower surfaces: Smooth, velvety. Color: When opening, upper surface: Upper lip petals: 84B; stripes, N89C. Lower lip petal: 76A. When opening, lower surface: 85C; stripes, 85A. Fully opened, upper surface: Upper lip petals: 75A; stripes, N88B; color becoming closer to 77C with development. Fully opened, lower surface: 76C to 76D. Nectar guide: Close to 4A. Nectar spur, when opening: 145C. Nectar spur, fully opened: 145C to 145D.

*Sepals.*—Quantity: Five-parted, star-shaped calyx. Shape: Lanceolate. Apex: Acute. Base: Truncate. Margin: Entire. Length: About 1.5 to 2 mm. Diameter: About 1 mm. Texture, upper and lower surfaces: Smooth, glabrous. Color, immature, upper and lower surfaces: 138A. Color, mature, upper and lower surfaces: 138A.

*Pedicels.*—Length: About 8 to 10 mm. Diameter: About 0.5 to 1 mm. Strength: Strong. Angle: About 35 to 45° from the stem. Texture: Smooth, glabrous. Color: 144A.

*Androecium.*—Stamen number: Two per flower. Anther shape: Rounded. Anther length: Less than 0.5 mm. Anther color: 5A. Amount of pollen: Moderate. Pollen color: 5A.

*Gynoecium.*—Pistil number: One per flower. Pistil length: Less than 1 mm. Style length: Less than 1 mm. Style color: 144C. Stigma shape: Rounded. Stigma color: 5A. Ovary color: 144C.

*Seed.*—Length: About 3 mm. Diameter: About 2 mm. Color: 200D.

Disease/pest resistance: Plants of the new *Nemesia* have not been observed to be resistant to pathogens or pests common to *Nemesias*.

Temperature tolerance: Plants of the new *Nemesia* have been observed to be tolerant to temperatures ranging from 0° to 40° C.

It is claimed:

1. A new and distinct cultivar of *Nemesia* plant named 'Sumnem 03', as illustrated and described.

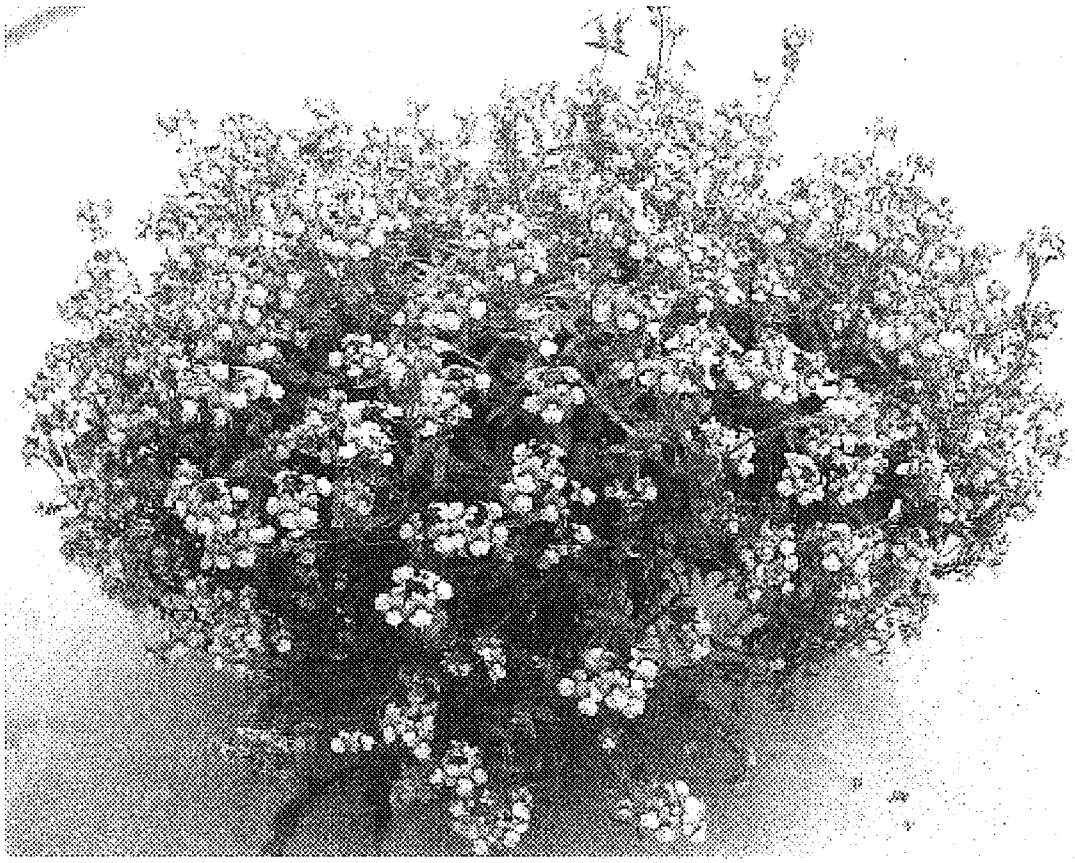

* * * * *